United States Patent [19]

Salka et al.

[11] Patent Number: 5,529,721
[45] Date of Patent: Jun. 25, 1996

[54] LIQUID PEARLIZING COMPOSITION

[75] Inventors: Barry A. Salka, Fair Lawn; Bruce W. Gesslein, Brick, both of N.J.; Robert M. Jablonski, Brooklyn, N.Y.

[73] Assignee: Henkel Corporation, Plymouth Meeting, Pa.

[21] Appl. No.: 287,975

[22] Filed: Aug. 9, 1994

Related U.S. Application Data

[63] Continuation-in-part of Ser. No. 49,214, Apr. 20, 1993, abandoned.

[51] Int. Cl.[6] .................. C11D 1/90; C11D 1/94; C11D 1/04; C11D 3/22
[52] U.S. Cl. .............. 252/546; 252/174.17; 252/170; 252/108; 252/DIG. 13
[58] Field of Search .............. 252/546, 174.17, 252/DIG. 13, 170, 108

[56] References Cited

U.S. PATENT DOCUMENTS

| | | | |
|---|---|---|---|
| 3,928,251 | 12/1975 | Bolich, Jr. et al. | 252/545 |
| 4,329,334 | 5/1982 | Su et al. | 424/70 |
| 4,565,647 | 1/1986 | Llenado | 252/354 |
| 4,599,188 | 7/1986 | Llenado | 252/174.17 |
| 4,663,069 | 5/1987 | Llenado | 252/117 |
| 4,842,850 | 6/1989 | Vu | 424/70 |
| 4,938,888 | 7/1990 | Kiefer | 252/91 |
| 5,057,311 | 10/1991 | Kamegai et al. | 424/70 |
| 5,099,065 | 3/1992 | Kubo et al. | 562/564 |
| 5,266,690 | 11/1993 | McCurry, Jr. et al. | 536/18.6 |

*Primary Examiner*—Erin M. Harriman
*Attorney, Agent, or Firm*—Wayne C. Jaeschke; John E. Drach; Henry E. Millson, Jr.

[57] ABSTRACT

A pearlizing agent for such products as shampoos and hand soaps contains a glycol distearate, an alkyl polyglycoside, a betaine of the formula II $$R^5-CONH-R^6-\underset{\underset{R^4}{|}}{\overset{\overset{R^3}{|}}{N^+}}-CH_2-CO_2^- \quad (II)$$

wherein $R^5$ is an alkyl or alkenyl group having from 7 to 21 carbon atoms and $R^6$ is alkylene group having from 2 or 3 carbon atoms; each of $R^3$ and $R^4$ is independently an alkyl group having from 1 to 4 carbon atoms, a glycol, and water.

12 Claims, No Drawings

LIQUID PEARLIZING COMPOSITION

CROSS REFERENCE TO RELATED APPLICATIONS

This application is a continuation-in-part of application Ser. No. 08/049,214 filed Apr. 20, 1993, now abandoned, the contents of which are fully incorporated herein by reference.

BACKGROUND OF THE INVENTION

1. Field of the Invention

This invention relates to liquid pearlizing agents which are useful in imparting pearlescence to personal care product formulations such as shampoos and the like.

2. Description of the Related Art

Pearlizing agents are additives used in personal care products such as shampoo, liquid hand soaps, shaving preparations and shower and bath products. Pearlizing agents impart a creamy, rich texture to the products into which they are incorporated and help in masking the presence of other additives such as anti-dandruff agents and polymeric conditioners in shampoos. Typically, pearlizing agents are solid materials such as glycol distearate, stearic acid, and glyceryl stearate. The incorporation of such materials into personal care products is often difficult and normally requires simultaneous heating and very efficient mixing. In spite of the measures taken to insure incorporation, existing pearlizing substances usually separate from the liquid phase as a solid or semi-solid material.

The compositions according to the invention alleviate the problems normally encountered in the use of existing pearlizing agents. The compositions according to the invention behave as nonionic liquids which are readily incorporated into personal care product formulations to provide stable liquids having good pearl and luster without a reduction in the foaming characteristics or viscosity. In fact, the compositions according to the invention help to increase the viscosity of formulations into which they are included.

SUMMARY OF THE INVENTION

It is has been surprisingly discovered that liquid compositions containing: (1) typical pearlizing agents such as glycol distearate, stearic acid, and glyceryl stearate; (2) a compound of the formula I $$R_1O(Z)_a \quad I$$

wherein $R_1$ is a monovalent organic radical having from about 6 to about 30 carbon atoms; Z is saccharide residue having 5 or 6 carbon atoms; a is a number having a value from 1 to about 6; (3) a betaine of the formula II $$R^5-CONH-R^6-\overset{\overset{R^3}{|}}{\underset{\underset{R^4}{|}}{N^+}}-CH_2-CO_2^- \quad (II)$$

wherein $R^5$ is an alkyl or alkenyl group having from 7 to 21 carbon atoms and $R^6$ is alkylene group having from 2 or 3 carbon atoms; each of $R^3$ and $R^4$ is independently an alkyl group having from 1 to 4 carbon atoms; (4) a glycol, and (5) water can be incorporated into personal care products such as shampoos. These liquid compositions allow the incorporation of the pearlizing agents contained therein at room temperature and with the use of normal mixing equipment and, if desired, in a continuous manner. The compositions according to the invention behave as nonionic liquids which can be used over a wide pH range and are compatible with formulations containing nonionic, anionic, cationic, and amphoteric surfactants.

DESCRIPTION OF THE PREFERRED EMBODIMENTS

Other than in the operating examples, or where otherwise indicated, all numbers expressing quantities of ingredients or reaction conditions used herein are to be understood as modified in all instances by the term "about".

The alkyl polyglycosides which can be used in the pearlizing compositions according to the invention have the formula I $$R_1O(Z)_a \quad I$$

wherein $R_1$ is a monovalent organic radical having from about 6 to about 30 carbon atoms; Z is saccharide residue having 5 or 6 carbon atoms; a is a number having a value from 1 to about 6. These alkyl polyglycosides are commercially available, for example, as APG®, Glucopon®, or Plantaren® surfactants from Henkel Corporation, Ambler, Pa., 19002. Examples of such surfactants include but are not limited to:

1. APG® 225 Surfactant—an alkylpolyglycoside in which the alkyl group contains 8 to 10 carbon atoms and having an average degree of polymerization of 1.7.

2. APG® 425 Surfactant—an alkyl polyglycoside in which the alkyl group contains 8 to 16 carbon atoms and having an average degree of polymerization of 1.6.

3. APG® 625 Surfactant—an alkyl polyglycoside in which the alkyl groups contains 12 to 16 carbon atoms and having an average degree of polymerization of 1.6.

4. APG® 325 Surfactant—an alkyl polyglycoside in which the alkyl groups contains 9 to 11 carbon atoms and having an average degree of polymerization of 1.6.

5. Glucopon® 600 Surfactant—an alkyl polyglycoside in which the alkyl groups contains 12 to 16 carbon atoms and having an average degree of polymerization of 1.4.

6. Plantaren® 2000 Surfactant—a $C_{8-16}$ alkyl polyglycoside in which the alkyl group contains 8 to 16 carbon atoms and having an average degree of polymerization of 1.4.

7. Plantaren® 1200 Surfactant—a $C_{12-16}$ alkyl polyglycoside in which the alkyl groups contains 12 to 16 carbon atoms and having an average degree of polymerization of 1.4.

Other examples include alkyl polyglycoside surfactant compositions which are comprised of mixtures of compounds of formula I wherein Z represents a moiety derived from a reducing saccharide containing 5 or 6 carbon atoms; a is zero; and $R_1$ is an alkyl radical having from 8 to 20 carbon atoms. The compositions are characterized in that they have increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions, also known as peaked alkyl polyglucosides, can be prepared by separation of the monoglycoside from the original reaction mixture of alkyl monoglycoside and alkyl polyglycosides after removal of the alcohol. This separation may be carried out by molecular distillation and normally results in the removal of about 70–95% by weight of the alkyl monoglycosides. After removal of the alkyl monoglycosides, the relative distribution of the various components, mono- and poly-glycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in U.S. Pat. No. 5,266,690, the entire contents of which are incorporated herein by reference.

The amount of the alkyl polyglycoside which can be used in the composition according to the invention can range from 1% to 75% by weight.

The pearlizing agents which can be used in the compositions according to the invention are stearic acid or polyol esters of stearic acid such as ethylene glycol distearate, 1,2-propylene glycol distearate, 1,2-1,3- and 1,4-butylene glycol distearate, glyceryl mono-, di-, and tri-stearate, polyethylene glycol distearate, and the like. The preferred pearlizing agents are ethylene glycol monostearate and ethylene glycol distearate. The amount of the pearlizing agent which can be used in the composition according to the invention can range from 5% to 40% by weight.

The betaines which can be used in the compositions according to the invention have the formula II

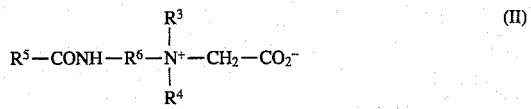

wherein $R^5$ is an alkyl or alkenyl group having from 7 to 21 carbon atoms and $R^6$ is alkylene group having from 2 or 3 carbon atoms; each of $R^3$ and $R^4$ is independently an alkyl group having from 1 to 4 carbon atoms. The preferred betaines are those wherein $R^3$ is an alkyl or alkenyl group having from 10–12 carbon atoms, $R^4$ is alkylene group having from 2 or 3 carbon atoms; and each of $R^5$ and $R^6$ is a methyl group. The most preferred betaine is cocoamidopropyl betaine wherein $R^5$ is an alkyl group having 11 carbon atoms, $R^6$ is alkylene group having from 3 carbon atoms; and each of $R^4$ and $R^5$ is a methyl group. The amount of the betaine which can be used in the composition according to the invention can range from 1% to 15% by weight. The amount of betaine is dependent upon the amount of alkyl polyglycoside such that the alkyl polyglycoside/betaine weight ratio is always from 1/1 to 5/1.

The glycols which can be used in the compositions according to the invention are diols having from 2 to 4 carbon atoms such as ethylene glycol, 1,2- and 1,3-propylene glycol and 1,2-, 1,3-, and 1,4-butylene glycol. The preferred glycol is 1,2-propylene glycol. The amount of the glycol which can be used in the composition according to the invention can range from 1% to 15% by weight.

The amount of the water which can be used in the composition according to the invention can range from 0.1% to 60% by weight.

The compositions according to the invention are typically added to personal care products such as shampoo, liquid hand soaps, shaving preparations, shower and bath products, and the like in any amount which is effective in producing a pearlescent appearance or pearl character. Such an effective amount will vary with the type of personal care product but will typically range from 2% to 10% by weight in order to impart a soft, silvery, and pearly luster to such formulations.

The following examples are meant to illustrate but not to limit the invention.

EXAMPLE 1

A typical composition according to the invention was composed of the following: 30 parts of a $C_{12-16}$ alkyl polyglycoside in which the alkyl groups contains 12 to 16 carbon atoms and having an average degree of polymerization of 1.4, available commercially as Plantaren™ 1200 surfactant (50% actives); 27.9 parts of water; 7.0 parts of 1,2-propylene glycol; 20.0 parts of Emerest® 2355, ethylene glycol distearate (a trademark product of Henkel Corporation, Emery group, Cincinnati, Ohio); 15.0 parts of Velvetex® BA-35 cocoamidopropyl betaine (30% actives, a trademark product of Henkel Corporation, Ambler, Pa.), and 0.1 parts of sodium hydroxide. The weight ratio of alkyl polyglycoside/betaine in this formulation is 3/1.

COMPARATIVE EXAMPLE 1

This example shows the effect of increasing the amount of betaine relative to the amount of alkyl polyglycoside on the ease of incorporation of three formulations used as a pearlizing agent for shampoo wherein the alkyl polyglycoside/betaine surfactant ratio is equal to 1/2.5. All amounts are in weight percent.

| Ingredient | A | B | C |
|---|---|---|---|
| APG ® surfactants[2] | 5 | 7.5 | 7 |
| Betaine[1] | 13 | 20 | 18 |
| APG/Betaine | 1/1.56 | 1/1.6 | 1/1.54 |
| H$_2$O | 81 | 52.5 | 48 |
| PG[3] | — | — | 7 |
| GD[4] | 1 | 20 | 20 |

[1]Velvetex ® BA-35 surfactant
[2]Plantaren ™ 1200 surfactant
[3]1,2-propylene glycol
[4]Emerest ® 2355 glycol distearate Samples B–C were added to a commercial shampoo formulation which contains TEA lauryl sulfate, ammonium lauryl sulfate, lauramide DEA, sodium chloride, citric acid, hydroxypropyl methyl cellulose, palmitic acid, fragrance, a preservative and water at a 3% w/w level while the formulation from Example 1 and sample A were added to a synthetic shampoo formulation having the following composition (in % w/w): 5.0% NaCl, 58.5% water, 25% Texapon ASV, 6.5% Velvetex® BA-35, at the 5% level and observations for pearl and ease of dispersion were made for each. The following observations were made on the shampoo formulations containing the various pearlizing additives. The shampoo formulation containing the pearlizing agent designated as Sample 1 gave a pearlescent appearance and had a viscosity (Brookfield RV, spindle #5 @20 rpm) of 3,720 cps. The shampoo formulation containing the pearlizing agent designated as Sample A was opaque and exhibited no pearlescence and had a viscosity (Brookfield RV, spindle #5 @20 rpm) of 1,280 cps. The shampoo formulation containing the pearlizing agent designated as Sample B was difficult to disperse, several agglomerations were noticed throughout as the pearlizing agent was being stirred into the shampoo. Incorporation of the pearlizing agent took more than 10 minutes and the final product was opaque and exhibited no pearlescence. The shampoo formulation containing the pearlizing agent designated as Sample C was moderately easy to disperse requiring only 5 minutes incorporation time. Although pearl developed with good intensity, the final product was too dense to be acceptable. The behavior of Sample C illustrates the effect of the incorporation of propylene glycol into a pearlescent concentrate having a betaine/alkyl polyglycoside surfactant ratio is equal to 2.5/1.

COMPARATIVE EXAMPLE 2

The following table of data shows the effect of the alkyl polyglycoside/betaine ratio in various liquid pearlizing agents on their viscosity in cps (Brookfield RV, spindle #5 @20 rpm) and the ease of incorporation of 5% by weight of the liquid pearlizing agent into a 10% by weight aqueous sodium lauryl sulfate solution at room temperature and the pearlescent appearance of the resulting formulation.

Each of the following liquid pearlizing compositions listed in the table below were comprised of: (a) 20% by weight of the total of Plantaren® 1200 Surfactant (50% actives) and Velvetex® BA-35 cocoamidopropyl betaine (30% actives), 7% by weight of 1,2-propylene glycol; 20% by weight of Emerest® 2355 glycol distearate; and sufficient water to achieve a total of 100%.

| Sample | APG/Betaine | Viscosity | Pearl Character | Dissolution Ease |
|--------|-------------|-----------|-----------------|------------------|
| D | 1/4 | 22000 | good | difficult |
| E | 1/3 | 15500 | good | difficult |
| F | 1/2 | 12500 | good | easy |
| G | 1/1 | 9500 | good | easy |
| H | 2.5/1 | 8550 | good | easy |
| I | 3/1 | 8500 | good | easy |
| J | 3.3/1 | 7680 | good | easy |
| K | 4/1 | 7600 | good | easy |
| L | 5/1 | 3800 | good | easy |

Those formulations having an alkyl polyglycoside/betaine ratio equal to at least 1/1 was also easily incorporated into a formulation at room temperature and gave good pearl character. In addition, formulations having an alkyl polyglycoside/betaine ratio equal to at least 1/1 also exhibited viscosities of less than 10,000 cps @25° C. which permits them to be readily flowable and pumpable under normal handling conditions.

What is claimed is:

1. A composition comprising: (1) from about 5% to about 40% by weight of a pearlizing agent selected from the group consisting of stearic acid and a polyol ester of stearic acid; (2) from about 1% to about 75% by weight of a compound of the formula I $$R_1O(Z)_a \quad I$$

wherein $R_1$ is a monovalent organic radical having from about to about 30 carbon atoms; Z is saccharide residue having 5 or 6 carbon atoms; a is a number having a value from 1 to about 6; (3) from about 1% to about 15% by weight of a betaine of the formula II $$R^5-CONH-R^6-\underset{\underset{R^4}{|}}{\overset{\overset{R^3}{|}}{N^+}}-CH_2-CO_2^- \quad (II)$$

wherein $R^5$ is an alkyl or alkenyl group having from 7 to 21 carbon atoms and $R^6$ is alkylene group having from 2 or 3 carbon atoms; each of $R^3$ and $R^4$ is independently an alkyl group having from 1 to 4 carbon atoms; (4) from about 1% to about 15% by weight of a glycol, and (5) from about 0.1% to about 60% by weight of water; wherein the weight ratio of said compound of the formula I to said betaine is from 1/1 to 5/1.

2. The composition of claim 1 wherein said compound of the formula I is a $C_{12-16}$ alkyl polyglycoside having an average degree of polymerization of about 1.4.

3. The composition of claim 1 wherein said compound of the formula II is cocoamidopropyl betaine.

4. The composition of claim 1 wherein said glycol is 1,2-propylene glycol.

5. A composition comprising: (1) from about 5% to about 40% by weight of a pearlizing agent selected from the group consisting of stearic acid and a glycol distearate; (2) from about 1% to about 75% by weight of a $C_{12-16}$ alkyl polyglycoside having an average degree of polymerization of about 1.4; (3) from about 1% to about 15% by weight of a cocoamidopropyl betaine; (4) from about 1% to about 15% by weight of 1,2-propylene glycol; and (5) from about 0.1% to about 60% by weight of water; wherein the weight ratio of said alkyl polyglycoside to said betaine is from 1/1 to 5/1.

6. A composition comprising: (1) from about 15% to about 20% by weight of a $C_{12-16}$ alkyl polyglycoside having an average degree of polymerization of 1.4; (2) about 45% to about 60% by weight of water; (3) about 5% to about 10% by weight of 1,2-propylene glycol; (4) about 15% to about 30% % by weight of ethylene glycol distearate; (5) about 4% to about 15% by weight of cocoamidopropyl betaine; and (6) about 0.1% to about 1% by weight of sodium hydroxide.

7. A process for producing a pearlescent personal care product which comprises adding to a personal care product an effective amount of a liquid pearlizing composition comprising: (1) a pearlizing agent selected from the group consisting of stearic acid and a polyol ester of stearic acid; (2) a compound of the formula I $$R_1O(Z)_a \quad I$$

wherein $R_1$ is a monovalent organic radical having from about 6 to about 30 carbon atoms; Z is saccharide residue having 5 or 6 carbon atoms; a is a number having a value from 1 to about 6;(3) from about 1% to about 15% by weight of a betaine of the formula II $$R^5-CONH-R^6-\underset{\underset{R^4}{|}}{\overset{\overset{R^3}{|}}{N^+}}-CH_2-CO_2^- \quad (II)$$

wherein $R^5$ is an alkyl or alkenyl group having from 7 to 21 carbon atoms and $R^6$ is alkylene group having from 2 or 3 carbon atoms; each of $R^3$ and $R^4$ is independently an alkyl group having from 1 to 4 carbon atoms; (4) from about 1% to about 15% by weight of a glycol, and (5) from about 0.1% to about 60% by weight of water; wherein the weight ratio of said compound of the formula I to said betaine is from 1/1 to 5/1.

8. The process of claim 7 wherein said compound of the formula I is a $C_{12-16}$ alkyl polyglycoside having an average degree of polymerization of about 1.4.

9. The process of claim 7 wherein said compound of the formula II is cocoamidopropyl betaine.

10. The process of claim 7 wherein said glycol is 1,2-propylene glycol.

11. The process of claim 7 wherein said personal care product is a shampoo.

12. The process of claim 7 wherein the effective amount of said liquid pearlizing composition is from about 2% to about 10% by weight.

* * * * *